United States Patent [19]
Lococo

[11] Patent Number: 4,828,496
[45] Date of Patent: May 9, 1989

[54] ENDODONTIC CORE ASSEMBLY

[76] Inventor: Michael P. Lococo, 4999 Victoria Avenue, Niagara Falls, Ontario, Canada, L3E 4C9

[21] Appl. No.: 147,276

[22] Filed: Jan. 22, 1988

[51] Int. Cl.⁴ .............................................. A65C 5/02
[52] U.S. Cl. ..................................... 433/224; 433/221
[58] Field of Search ........................ 433/220, 221, 224

[56] References Cited

U.S. PATENT DOCUMENTS

| | | | |
|---|---|---|---|
| 430,522 | 6/1890 | Genese | 433/221 |
| 1,139,028 | 5/1915 | Gibson | 433/221 |
| 4,349,336 | 9/1982 | Weissmann . | |

FOREIGN PATENT DOCUMENTS

| | | | |
|---|---|---|---|
| 87908 | 6/1904 | Canada . | |
| 170683 | 7/1916 | Canada . | |
| 406020 | 7/1942 | Canada . | |
| 958261 | 11/1974 | Canada . | |
| 1008138 | 4/1977 | Canada . | |
| 1055742 | 6/1979 | Canada . | |
| 1084202 | 8/1980 | Canada . | |
| 1111681 | 11/1981 | Canada . | |
| 1121617 | 4/1982 | Canada . | |
| 1132381 | 9/1982 | Canada . | |
| 126184 | 1/1901 | Fed. Rep. of Germany | 433/220 |

Primary Examiner—Robert Peshock
Attorney, Agent, or Firm—Stevens, Davis, Miller & Mosher

[57] ABSTRACT

Endodontic core and post are disclosed, forming an integral unit of which the post, adapted to be anchored in the respective root canal, is provided with, preferably, four wings perforated to allow passage of cement or the like through same in order to enhance the strength of embedding of the post in the root canal. The radial wings of the post are disposed each in a recess which is reamed by utilizing a special guiding post which is also a part of the present invention. In order to further enhance the strength of the bond between the core and the post in the respective root canal, an extension beam, preferably of a cross-shaped cross-sectional configuration, is adhesively secured to the free end of the post to form a "winged" extension of the post itself. The wings of the beam extension are also perforated for the same reason.

21 Claims, 1 Drawing Sheet

ENDODONTIC CORE ASSEMBLY

BACKGROUND OF THE INVENTION

The present invention relates to an endodontic core assembly. Endodontic core assemblies are used in providing a core or anchor for an artificial tooth or the like. The core is usually integral with a post which is normally adapted to be inserted in and fixedly secured to the root canal of a tooth, the root canal usually requiring a preliminary preparation by a reamer.

Since the core is normally exposed to very substantial loads both torsional and flexing, it is very important that the post be embedded within the root canal as firmly as possible. Three basic systems are known for this purpose: The first system is a threaded post, which is usually combined with a suitable cement to secure a firm hold within the root canal. The second known system is a frictional arrangement which is somewhat similar to the threaded system in that the side walls of the root canal are frictionally engaged by the post and the overall bond is further improved by the use of cement. The third known system is so-called cemented system in which the post is made such as to be relatively loose in the root canal and is secured to the root canal walls solely by a suitable cement filling the space between the canal and the post.

Of the above-mentioned three systems, the threaded and frictional system are disadvantageous in that they require a relatively substantial pressure to be exerted upon the inside wall of the root canal engaged by the post. Such forces are directed generally radially outwardly and may result in undesired damage to the root canal which in turn, may give rise to reduced strength of the overall hold of the post (and thus the core) in the root canal.

From the standpoint of avoiding excessive radial pressures on the root canal walls, the cemented arrangement appears to be better advantaged than the first two since there is no active pressure exerted upon the walls of the canal. On the other hand, the canal being usually somewhat conical and usually decreasing in width with the increasing depth of the canal, the problem is to provide a reasonably strong hold by merely the cementing of the post within the prepared root canal. In practice, the cemented version therefore suffers from the drawback of a reduced strength of the anchoring of the post within the canal, the reduction in the strength of the hold being a trade-off for the elimination of the undesired radial stress to which the root canal is subjected with the first two systems. The present invention relates to the third mentioned group, i.e. to the cemented systems.

SUMMARY OF THE INVENTION

It is an object of the present invention to provide improvement in the art of the "cemented" endodontic core assemblies in which the side walls of the root canal prepared for receiving a post are still generally free of any radially outward pressures while the hold of the post within the root canal is improved.

In general terms, the present invention provides an endodontic core assembly comprising, in combination: a core; a post forming a generally cylindrical extension of the core and being integral with same; said post comprising a solid central section and a plurality of winged sections protruding radially away from the central section, over generally the entire length of the post.

In accordance with another feature of the present invention, each wing is provided with a number of transverse passages for allowing a cement mixture to penetrate each wing section to improve the strength of anchoring of the post in a respective root canal. The post may be provided with a beam attachment means, said beam attachment means being disposed at a free end portion of the central section, said free end portion being remote and facing away from the core.

In accordance with a still further feature of the present invention, the assembly comprises a beam extension member fixedly secured to the central section at said beam attachment means to form a generally co-axial extension of said post, whereby said beam extension can occupy that part of the length of a respective root canal which is not occupied by the said post.

In another aspect of the present invention, a kit is provided for the production and installing of an endodontic core. The kit comprises a core member including a core and a post forming a generally cylindrical extension of the core and being integral with same, said post comprising a core member including a core and a post forming a generally cylindrical extension of the core and being integral with same, said post comprising a solid central section and a plurality of winged sections protruding radially away from the central section and extending over generally the entire length of the post; beam attachment means disposed at a free end portion of said central section, said free end portion being remote from the core and facing away from same; extension beam means complementary with the beam attachment means for permanent securement of the beam means to said central section.

BRIEF DESCRIPTION OF THE DRAWINGS

The invention will now be described by way of an exemplary embodiment with reference to the accompanying drawings in which.

DETAILED DESCRIPTION OF AN EXEMPLARY EMBODIMENT

Figure 1:
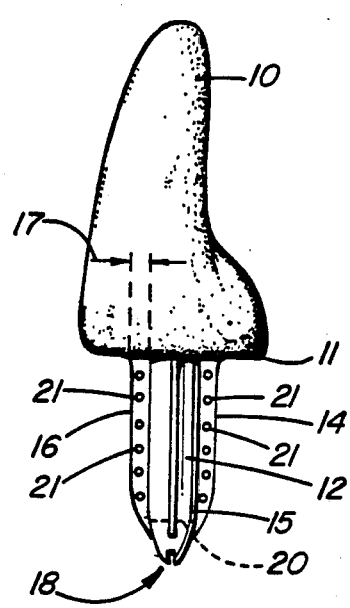
FIG. 1 is a side view an endodontic core assembly showing one aspect of the present invention.
Figure 2:
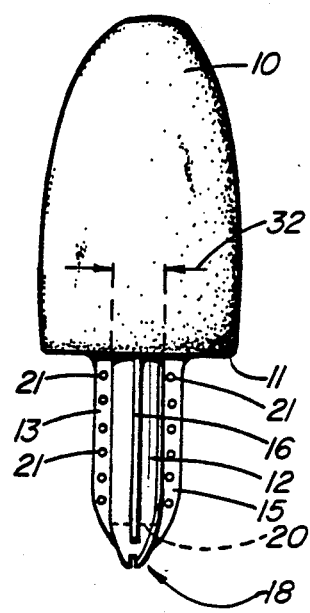
FIG. 2 is a view taken from the left-hand side of FIG. 1.
Figure 3:
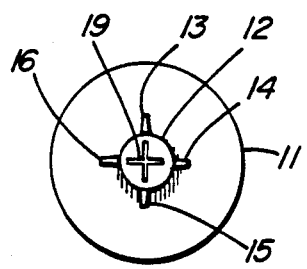
FIG. 3 is a simplified, not-to-scale bottom view of FIG. 1.

Turning now to FIG. 1 and FIG. 2, and also referring to the view of FIG. 3, a typical endodontic core assembly comprises an integral piece as shown which has a core 10 normally providing the anchoring surface for an artificial tooth or the like. The periphery 11 of the core 10 normally has a diameter greater than that of a generally cylindric post 12 whose lowermost end is beveled so that the overall configuration of the post 12 is somewhat conical. According to the present invention, the generally cylindric post 12 is formed by a central section to which the lead lines of reference numeral 12 are directed and by four wing sections 13, 14, 15 and 16. The width of the wing sections 13–16 as measured radially of elongation of the post 12 is the same and is referred to with reference numeral 17 in FIG. 1. At the free end 18 of the post 12, which is remote and turned away from the core 10, a cross-shaped cutout 19 is provided (FIG. 3). The depth of the cutout is indicated by a broken line 20, shown in FIGS. 1 and 2 and indicating the bottom of the cross-shaped cutout 19. It is further shown in FIGS. 1 and 2 that each of the winged sections 13–16 is provided with a plurality of transverse passages or openings 21. The purpose of the passages 21 is to allow penetration of the wing sections 13–16 by cement or the like when the post is installed in a root canal as will be explained hereinafter.

Figure 4:
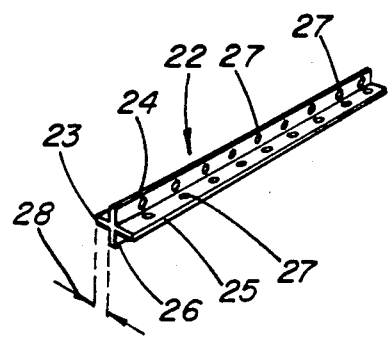
FIG. 4 is a perspective view of a length of a rod used in producing beam attachment means of the present invention.

Turning now to FIG. 4, a cross-shaped stem 22 is shown. The stem defines four wings 23, 24, 25 and 26 which are disposed about a solid center of the stem or rod and protrude radially from same, as best seen from the cross-sectional shape which is apparent at the forward end of the rod 22 as viewed in FIG. 4. The wings 23–26 are also provided each with a number of openings or passages 27. The width 28 (FIG. 4) of each of the wings 23–26 is the same. The cross-sectional configuration of the cutout 19 is designed such that the cutout 19 can receive one end of the rod 22. It will be appreciated that a number of relatively short lengths can be cut off the rod 22 for the respective core and post members. Furthermore, the rod 22 designates only one size of an extension stem, it being understood that different sizes are normally provided for different sizes of the post 12 depending on the particular application.

The size of the cutout 19 is preferably so designed that a close fit exists between the cutout 19 and the end of the member cut off from the rod 22. The mutual securement can be obtained, for instance, by a suitable adhesive such as "Krazy Glue" (a trademark).

Those skilled in the art of dentistry will also immediately recognize that the edges of the Wings 23–26 can be machined or otherwise treated to conform to the downwardly narrowing shape, Of a prepared root canal.

Figure 5:
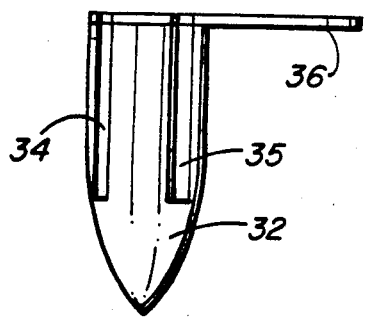
FIG. 5 is a side view of a reamer guide used in reaming a root canal to produce guide grooves for the post.
Figure 6:
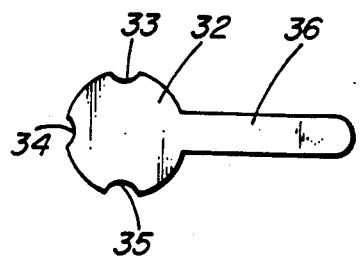
FIG. 6 is a top plan view of the tool of FIG. 5.
Figure 7:
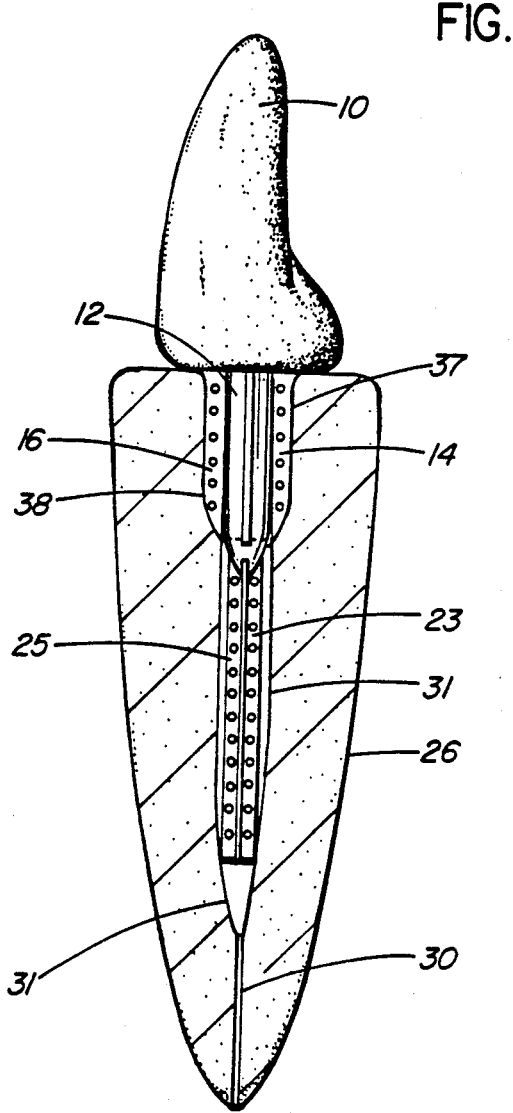
FIG. 7 is a diagramatic side view of a core and post together with a beam extension located in a root canal.

Reference may now be had to FIG. 7 which shows in a diagramatic way a root 26. As is well know, each root has a root canal 30 disposed generally centrally of the root 28 and in a healthy tooth serving the purpose of providing passage for the nerve of the respective tooth. When utilizing the present invention, the nerve is no longer present in the canal and the canal 30 is widened by a suitable reamer such as to provide a generally circular and slightly downwardly narrowing passage 31 whose upper diameter normally corresponds to the diameter 32 of (FIG. 2) the post 12, it being understood that the passage 31 is generally circular at any cross-sectional level thereof. After preparing the passage 31, the tool of FIG. 5 is to be applied. The tool comprises a generally cylindric or slighty conical body or core 32 whose diameter corresponds to that of the reamed passage 31 at the upper end thereof. In other words, the body 32 generally corresponds to the size and shape of the post 12. The periphery of the body 32 is provided with three concavely shaped grooves 33, 34 and 35 (FIG. 6). Reference numeral 36 designates a handle for manipulating the body 32 into and out of the reamed passage 31. It will be readily appreciated that with the body 32 receiving the reamed passage, the grooves 33, 34 and 35, which are disposed at 90° with respect to each other, provide a guiding surface for a smaller reamer for reaming grooves in the wall of the first mentioned passage 31 to accomodate the winged section 13–16 of the post 12. When the three openings are made, the body 32 is released and turned by 90° utilizing the handle 36. For instance, the turning can be made clockwise from the position shown in FIG. 6, whereupon the fourth groove in the wall of the passage 31 can be reamed utilizing once more the groove 33 of the body 32.

When the reaming is finished, the root canal is provided with four exterior grooves of which only two grooves 37 and 38 are shown in FIG. 7, to accomodate the wing sections 14 and 16, respectively, it being understood that the remaining wing sections 15 and 19 are disposed within the remaining two grooves produced by means of the tool shown in FIGS. 5 and 6. The width of the wings 23, 25 of the associated piece of the rod 22 is prepared such that the outer edges of the extension member generally conform to the configuration of the opening or passage 31.

As is well known, the prepared passage 31 can now be cleaned and filled with a suitable cement which can penetrate the passages 21 and 27 of the wing sections and wings to improve the bond of the post 12 with the root canal 30.

Basically, the combination of the wing sections 13–16 and of the grooves such as grooves 37, 38 provide resistance of the overall assembly against torsional stresses without the need for exerting undue radially outward pressure onto the inside walls of the reamed opening 31, while the extension beam portion secured to the free end of the post 12 very substantially increases the surface of what is now an integral part of the core 10 thus providing a firm hold against bending or pulling forces that may be active at the core 10.

Those skilled in the art will readily appreciate that many of the features described in the exemplary embodiment can be modified without departing from the scope of the present invention as recited in accompanying claims.

I claim:

1. Endodontic core assembly comprising, in combination:
   (a) a core;
   (b) a post forming an extension of the core and being integral with same;
   (c) said post comprising a solid, elongated, generally cylindrical central section and a plurality of winged sections protruding radially away form the central section over generally the entire length of the post, each winged section defining a longitudinal outer edge portion which, at any transverse reference plane perpendicular to the axis of the post, is more remote from the axis of the post than any other part of the post at that reference plane.

2. Endodontic core assembly as claimed in claim 1, wherein each winged section is provided with a number of transverse passages for allowing a cement mixture to penetrate each winged section to improve the strength of anchoring of the post in a respective root canal.

3. Endodontic core assembly as claimed in claim 1, wherein said post is provided with extension stem mounting means, for fixedly securing to the post, generally coaxially therewith, an extension stem at a free end portion of the central section remote from the core, to thus provide an integral extension of the post.

4. Endodontic core assembly as claimed in claim 3, further comprising an extension stem fixedly secured to the central section at said mounting means and forming a generally coaxial extension of said post, whereby the length at which the core can be anchored in a respective root canal is increased.

5. Endodontic core assembly as claimed in claim 4, wherein said extension stem includes an elongated central portion and a plurality of generally radial wing sections.

6. Endodontic core assembly as claimed in claim 5, wherein said beam mounting means includes a recess in said free end portion of the central section portion, said recess having cross-sectional configuration complementary with that of said extension stem.

7. Endodontic core assembly as claimed in claim 6, wherein one end of said extension stem is inserted in said recess and is adhesively secured to same.

8. Endodontic core assembly as claimed in claim 5, wherein said radial wing sections of the beam extension member are provided with a number of transverse passages for allowing a cement mixture to penetrate each wing section to improve the strength of anchoring of the extension stem in a respective root canal.

9. Endodontic core assembly as claimed in claim 8, wherein each wing section of said post is provided with a number of transverse passages for allowing a cement mixture to penetrate each wing section to improve the strength of anchoring of the post in a respective root canal.

10. Endodontic core assembly as claimed in claim 8, wherein the extension stem has four winged sections disposed in a cross-shaped cross-sectional pattern at a 90° spacing from each other.

11. Endodontic core assembly as claimed in claim 8, wherein the extension stem has four wing sections disposed in a cross-shaped cross-sectional pattern at a 90° spacing from each other, said post also having four wing sections disposed in a cross-shaped cross-sectional pattern at a 90° spacing from each other.

12. Endodontic core assembly as claimed in claim 1, wherein each longitudinal outer edge portion extends continuously over generally the entire length of the post.

13. Endodontic core assembly as claimed in claim 12, wherein the surface of the solid central section between adjacent winged sections is smooth, whereby a continuous channel extending along the entire length of the post is formed between each pair of adjacent ones of the winged sections.

14. A kit for the production of an endodontic core comprising:
  (a) a core member including a core and a post forming a generally cylindrical extension of the core and being integral with same, said post comprising a solid central section and a plurality of winged sections protruding radially away from the central section and extending over generally the entire length of the post;
  (b) beam attachment means disposed at a free end portion of said central section, said free end portion being remote from the core and facing away from same;
  (c) extension beam means complementary with the beam attachment means for permanent securement of the beam means to said central section.

15. A kit as claimed in claim 14, wherein the extension beam means is a length of a rod having cross-sectional configuration comprised of a central section and a number of radial wings, said beam attachment means being a cutout in the free end portion of said central section complimentary with the cross-sectional configuration of said rod, whereby a length of the rod can be cut off and one end of the cut off piece can be inserted in the cutout and adhesively secured to same.

16. A kit as claimed in claim 15, wherein said radial wings have each the same width as measured radially of the elongation of the extension beam means, the wings being spaced from each other at a generally uniform angular spacing.

17. A kit as claimed in claim 16, comprising two or more of said extension beam means differing from each other in said width of the wings.

18. A kit as claimed in claim 15, wherein said wings are perforated to provide passages therein for cement or the like to improve the strength of anchoring of the beam means in a respective root canal.

19. A kit as claimed in claim 14, wherein there are four wing sections protruding radially away from the central section, said wing sections being spaced from each other at a generally uniform, 90° spacing.

20. A kit as claimed in claim 19, wherein the width of said wing sections as measure radially of the post is the same at each wing sections.

21. A kit as claimed in claim 20, further comprising a reamer guidance insert including an elongated, conical core having a major diameter end a minor diameter end, said core further having longitudinal grooves in its surface, the size and shape of the core being generally the same as that of the respective central section, said grooves being concavely rounded in cross-section and being spaced from each other at an angular spacing corresponding to that of the wing sections of the post, and handle means for manipulating the guidance insert into and out of a reamed root canal prior to the reaming of passages for receiving the wing sections of the post.

* * * * *